(12) United States Patent
Willi et al.

(10) Patent No.: US 8,900,241 B2
(45) Date of Patent: Dec. 2, 2014

(54) INSTRUMENT FOR PREPARING AND/OR MACHINING A FEMORAL HEAD

(75) Inventors: Roland Willi, Neftenbach (CH); Marcel Hinder, St. Gallen (CH); Andreas Marchione, Winterthur (CH)

(73) Assignee: Zimmer GmbH, Winterthur (CH)

( * ) Notice: Subject to any disclaimer, the term of this patent is extended or adjusted under 35 U.S.C. 154(b) by 258 days.

(21) Appl. No.: 13/558,560

(22) Filed: Jul. 26, 2012

(65) Prior Publication Data

US 2012/0289967 A1 Nov. 15, 2012

Related U.S. Application Data

(63) Continuation of application No. 12/088,979, filed as application No. PCT/EP2006/067162 on Oct. 6, 2006, now Pat. No. 8,236,001.

(30) Foreign Application Priority Data

Oct. 6, 2005 (EP) .................................... 05021794

(51) Int. Cl.
*A61B 17/56* (2006.01)
*A61B 17/17* (2006.01)
*A61B 17/16* (2006.01)
*A61B 17/88* (2006.01)

(52) U.S. Cl.
CPC ........... *A61B 17/175* (2013.01); *A61B 17/1668* (2013.01); *A61B 17/8866* (2013.01)
USPC .............................. 606/86 R; 606/89; 606/96

(58) Field of Classification Search
USPC ...................... 606/86 R, 87–89, 96
See application file for complete search history.

(56) References Cited

U.S. PATENT DOCUMENTS

| 221,611 A | 11/1879 | Ringstad |
| 1,448,111 A | 3/1923 | Eppler |

(Continued)

FOREIGN PATENT DOCUMENTS

| DE | 1164019 B | 2/1964 |
| EP | 0992222 A2 | 4/2000 |

(Continued)

OTHER PUBLICATIONS

"U.S. Appl. No. 12/088,979, Final Office Action mailed Jun. 8, 2011", 19 pgs.

(Continued)

*Primary Examiner* — Nicholas Woodall
*Assistant Examiner* — Larry E Waggle, Jr.
(74) *Attorney, Agent, or Firm* — Schwegman Lundberg & Woessner, P.A.

(57) ABSTRACT

In some examples, a method for at least one of preparation or machining of a femoral head formed on a neck of a femur includes selecting an instrument including probing forceps and a guide element including a centering axis. The guide element is coupled to the probing forceps at first and second coupling points disposed along the centering axis such that the centering axis is disposed in a central plane of the probing forceps independent of an opening angle of the probing forceps. The probing forceps are closed with probing jaws symmetrically contacting the neck of the femur at opposite sides with respect to an axis of the neck of the femur. The guide element self-adjusts with closing of the probing forceps so that the centering axis is automatically aligned in the middle with respect to the two oppositely disposed sides of the neck of the femur.

20 Claims, 11 Drawing Sheets

(56) References Cited

U.S. PATENT DOCUMENTS

| | | |
|---|---|---|
| 3,960,147 A | 6/1976 | Murray |
| 4,896,663 A | 1/1990 | Vandewalls |
| 5,312,409 A | 5/1994 | McLaughlin et al. |
| 5,817,098 A | 10/1998 | Albrektsson et al. |
| 5,951,564 A | 9/1999 | Schroder et al. |
| 6,159,217 A | 12/2000 | Robie et al. |
| 7,022,141 B2 | 4/2006 | Dwyer et al. |
| 8,236,001 B2 | 8/2012 | Willi et al. |
| 2004/0220582 A1 | 11/2004 | Keller |
| 2005/0021042 A1 | 1/2005 | Marnay et al. |
| 2005/0033290 A1 | 2/2005 | Nevelos et al. |
| 2005/0049714 A1 | 3/2005 | Crofford |
| 2005/0113841 A1 | 5/2005 | Sheldon et al. |
| 2005/0245936 A1* | 11/2005 | Tuke et al. ............ 606/89 |
| 2006/0271058 A1 | 11/2006 | Ashton et al. |
| 2007/0162038 A1 | 7/2007 | Tuke |
| 2007/0162039 A1 | 7/2007 | Wozencroft |
| 2008/0183179 A1 | 7/2008 | Siebel et al. |
| 2008/0215057 A1 | 9/2008 | Willi et al. |

FOREIGN PATENT DOCUMENTS

| | | |
|---|---|---|
| EP | 0992222 A3 | 4/2000 |
| EP | 1477120 A1 | 11/2004 |
| EP | 1588669 A1 | 10/2005 |
| EP | 1477120 B1 | 2/2007 |
| EP | 1588669 B1 | 8/2007 |
| WO | WO-2006020655 A1 | 2/2006 |
| WO | WO-2006134345 A1 | 12/2006 |
| WO | WO-2007039647 A1 | 4/2007 |

OTHER PUBLICATIONS

"U.S. Appl. No. 12/088,979, Non Final Office Action mailed Sep. 1, 2011", 17 pgs.

"U.S. Appl. No. 12/088,979, Non-Final Office Action mailed Feb. 15, 2011", 18 pgs.

"U.S. Appl. No. 12/088,979, Notice of Allowance mailed Apr. 2, 2012", 12 pgs.

"U.S. Appl. No. 12/088,979, Preliminary Amendment filed Jun. 17, 2010", 53 pgs.

"U.S. Appl. No. 12/088,979, Response filed Jan. 24, 2012 to Non Final Office Action mailed Sep. 1, 2011", 9 pgs.

"U.S. Appl. No. 12/088,979, Response filed Apr. 29, 2011 to Non Final Office Action mailed Apr. 29, 2011", 8 pgs.

"European Application Serial No. 05021794.2, European Search Report mailed Mar. 31, 2006", 6 pgs.

"International Application Serial No. PCT/EP2006/067162, International Preliminary Report on Patentability mailed Aug. 6, 2007", 11 pgs.

"International Application Serial No. PCT/EP2006/067162, International Search Report mailed Jan. 16, 2007", 6 pgs.

"International Application Serial No. PCT/EP2006/067162, Written Opinion mailed Jan. 16, 2007", 5 pgs.

* cited by examiner

INSTRUMENT FOR PREPARING AND/OR MACHINING A FEMORAL HEAD

CROSS REFERENCE TO RELATED APPLICATIONS

This application is a continuation of U.S. application Ser. No. 12/088,979, filed on Apr. 2, 2008, which application is a nationalization under 35 U.S.C. §371 of PCT/EP2006/067162, filed Oct. 6, 2006, which claims priority to European Application No. 05021794.2 filed on Oct. 6, 2005, the disclosures of which are hereby explicitly incorporated herein by reference in their entirety.

SUMMARY

The invention relates to an instrument for the preparation and/or machining of a femoral head.

The femoral head is formed at the proximal end of a femur and forms a hip joint together with a hip joint socket of a pelvic bone. Prior to the insertion or mounting of an implant which at least partly replaces the femoral head the femoral head is prepared and/or machined by means of instruments of the initially named kind. The instruments serve in particular for the alignment of tools for the machining of the femoral head at the femoral head. The alignment as a rule takes place with reference to the neck of the femur. A machining of the femoral head matched to the respective patient is of particular importance in the case of a so-called "resurfacing" in which it is not the whole of the natural femoral head which is replaced but rather only an outer layer of bone material is removed in order to subsequently mount a cap-like femur implant on the remaining femur stump, with the femur implant cooperating with the hip joint socket of the pelvic bone, in particular with an artificial hip joint shell.

An instrument of the initially named kind is now proposed here which, in addition to a multitude of other advantageous characteristics, ensures a simple and at the same time precise alignment of a tool which is to be used subsequently for the machining of a femoral head. More specifically it should for example be possible to specify an axis, in particular a drilling axis for a tool for the machining of a femoral head. Furthermore, a method for the preparation and/or machining of a femoral head should be set forth.

In addition to other advantageous characteristics, the subjects described in the claims are able to fulfill these requirements.

The instrument set forth includes probing forceps having two forcep levers connected to one another at a point of rotation and also two probing jaws each associated with a respective one of the forcep levers. The instrument has a manipulation side and a working side with the probing jaws being arranged on the working side of the instrument. In addition a guide element having a central axis is provided. The guide element is supported and/or journalled and/or guided at at least two points mutually spaced apart on the direction of the central axis such that the central axis is always disposed in a central plane of the probing forceps independently of an opening angle of the probing forceps, said central plane including the fulcrum. The support and/or guide points are in this arrangement directly and/or indirectly pivotally connected to the probing forceps.

The forceps-like design of the instrument offers the operator an access "from above", i.e. at least approximately in the direction of the axis of the femur neck in that the probing jaws can be opened sufficiently far that they can pass by the femoral head. Working "from above" is extremely simple and above all only requires a little space. The subsequent probing of the femur neck takes place simply by closing the probing jaws. In this connection the operator can reliably probe the transition between the femoral head and the neck of the femur or the start of the neck in that he, for example, "travels" along the contour of the femur in the head region with the probing jaws as it were. For this purpose no space-consuming movements of the instrument are required but rather the instrument merely only needs to be opened and closed to a relatively small degree.

The probing jaws can for example be placed proximally and distally at the neck of the femur.

When the probing jaws contact the neck of the femur or the start of the neck it is automatically ensured that the axis of the neck of the femur extends at least approximately in the central plane of the instrument which extends through the fulcrum of the forceps levers and centrally between the probing jaws. In this way a center of the neck of the femur can be found, in particular in the proximal-distal direction and indeed independently of the width of the neck of the femur. Furthermore, as a result of the mounting and/or guidance of the guide elements it is automatically ensured that the central axis also lies in the central plane of the instrument, i.e. of the probing forceps. The central axis can for example determine a drilling axis for a drilling wire for a tool for the machining of the femoral head or a reference axis for such a drilling axis. Since both the axis of the neck of the femur and also the centering axis are located in the central plane of the probing forceps an alignment of the centering axis can be achieved with respect to the axis of the neck of the femur.

The above explained alignment of the instrument at the femur or the alignment of the centering axis with respect to the axis of the neck of the femur is in most cases regarded as a first alignment step, which can be followed, if required, by at least one further alignment step and/or at least one fine correction of the position of the instrument relative to the femoral head, or of the centering axis relative to the axis of the neck of the femur. Through the design of the instrument an ideal alignment in respect of the axis of the neck of the femur is always ensured, at least with respect to the central plane, in each position with the probing jaws contacting the neck of the femur or the start of the neck, whereby the alignment of the machining instruments which are to be used subsequently is considerably simplified for the operator.

In one embodiment a functional unit is provided which includes a drilling jig the drilling axis of which extends parallel to a lever plane spanned by the two forcep levers. After completed alignment of the instrument at the femur a bore coinciding with the drilling axis can in particular be formed in this manner in the femur head, into which a wire-like or bar-like element can then be introduced with the aid of which the machining tools, in particular milling cutters, can be guided in a reliable manner into an ideal orientation with respect to the position of the femoral cap relative to the femoral head and positioned and moved during the machining.

In one embodiment the forceps levers are rotatable relative to one another about a fixed axis of rotation and are additionally connected to one another at a distance from the axis of rotation via at least one articulated lever arrangement.

In a further embodiment the guide element on which the linear guide is formed carries the functional unit and connects the latter to the forcep levers. The linear guide is for example provided in the form of an elongate hole.

In a further embodiment the probing jaws are formed on pivotable end portions of the forcep levers. In this connection the pivotable end portions can be connected to one another via an articulated lever arrangement. This articulated lever arrangement can be provided in addition to an articulated lever arrangement disposed above the pivot region which in particular has a linear guide.

This articulated lever arrangement connecting the pivotable end sections to one another is executed in a further embodiment as a parallelogram linkage. In particular it is possible to achieve in this way a situation in which the pivotable end portions of the forcep levers—i.e. those parts of the pivotable end portions which are disposed parallel to a plane spanned by the forcep levers—always have the same orientation relative to one another and in particular extending parallel to one another during the opening and closing of the instrument independently of the opening width. For this purpose the space requirement of the instrument is minimized with optimized handling thereof.

The functional unit includes for example at least one aiming outrider which can be coupled with the at least one aiming bar in such a way that the aiming bar extends parallel to the centering axis. In this connection an aiming outrider can be pivotally designed and indeed about an axis which extends offset from and parallel to the centering axis or coincides with this axis.

In a further embodiment the instrument includes in particular the functional unit, a probing arm for the probing of the femur neck and/or of the transition between the femur head and the neck of the femur, with this probing arm being pivotable about the centering axis. With a probing arm of this kind "circular tracing" can be carried out whereby the operator can check the alignment of the instrument relative to the femur head while taking account of at least the substantial part of the total periphery.

In an exemplary embodiment aiming pins are attached to the probing jaws, with the connection line of the aiming pins standing perpendicular to the central plane and intersecting the central axis. These aiming pins enable a central position to be found in the neck region of the femoral head when the instrument is set in place.

In a further exemplary embodiment the instrument is provided with an adjustable auxiliary abutment with which an additional reference point can be provided for the operator during the alignment process. This auxiliary abutment can be adjustable in the central plane, for example in two directions which extend perpendicular to one another.

Further embodiments are set forth in the dependent claims, in the description and also in the drawing.

The various embodiments of an instrument that are set forth in accordance with the independent patent claim directed to the instrument, or the features realized there, can naturally be combined with one another.

In the method which is set forth for the preparation and or machining of a femoral head, which is formed on a neck of a femur which has a femur neck axis, an instrument is selected for the preparation and/or machining of the femoral head which includes probing forceps with two forcep levers and two probing jaws and also a guide element having a centering axis which always lies in a central plane of the probing forceps independently of an angle of opening of the probing forceps. The probing forceps are closed in such a way that the probing jaws symmetrically contact the neck of the femur on opposite sides with respect to the axis of the neck of the femur, in particular proximally and distally, whereby the centering axis is automatically aligned centrally with respect to the two oppositely disposed sides of the neck of the femur.

The invention will be explained in the following in more detail with reference to embodiments illustrated in the drawing. In this connection the embodiments in the drawing are only to be understood as instructive and are not to serve to restrict the subjects described in the claims. The representations in the drawings are simplified; details not necessary for an understanding of the invention have been omitted.

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION

Figure 1:
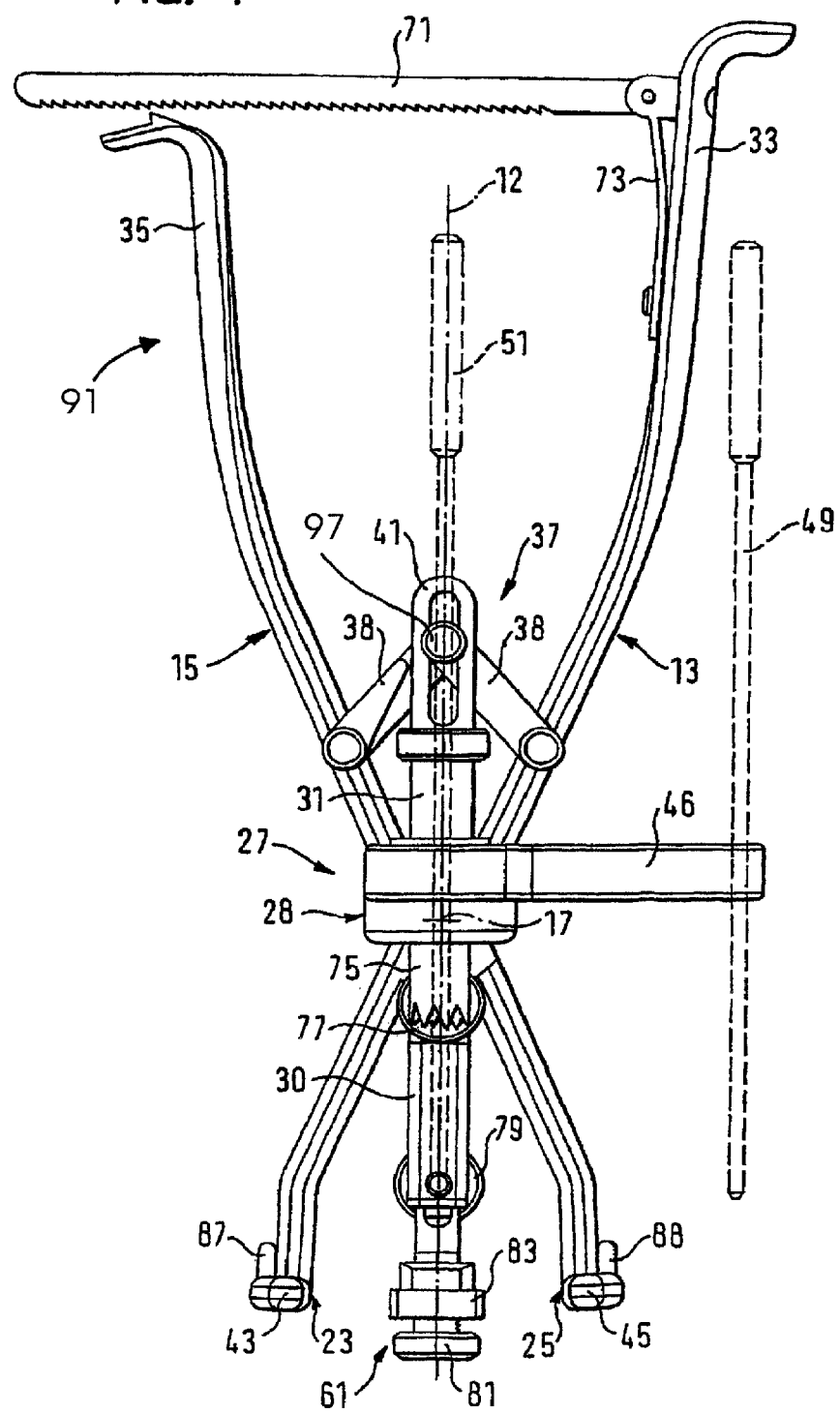
FIGS. 1-4 show various views of an embodiment of an instrument.
Figure 2:
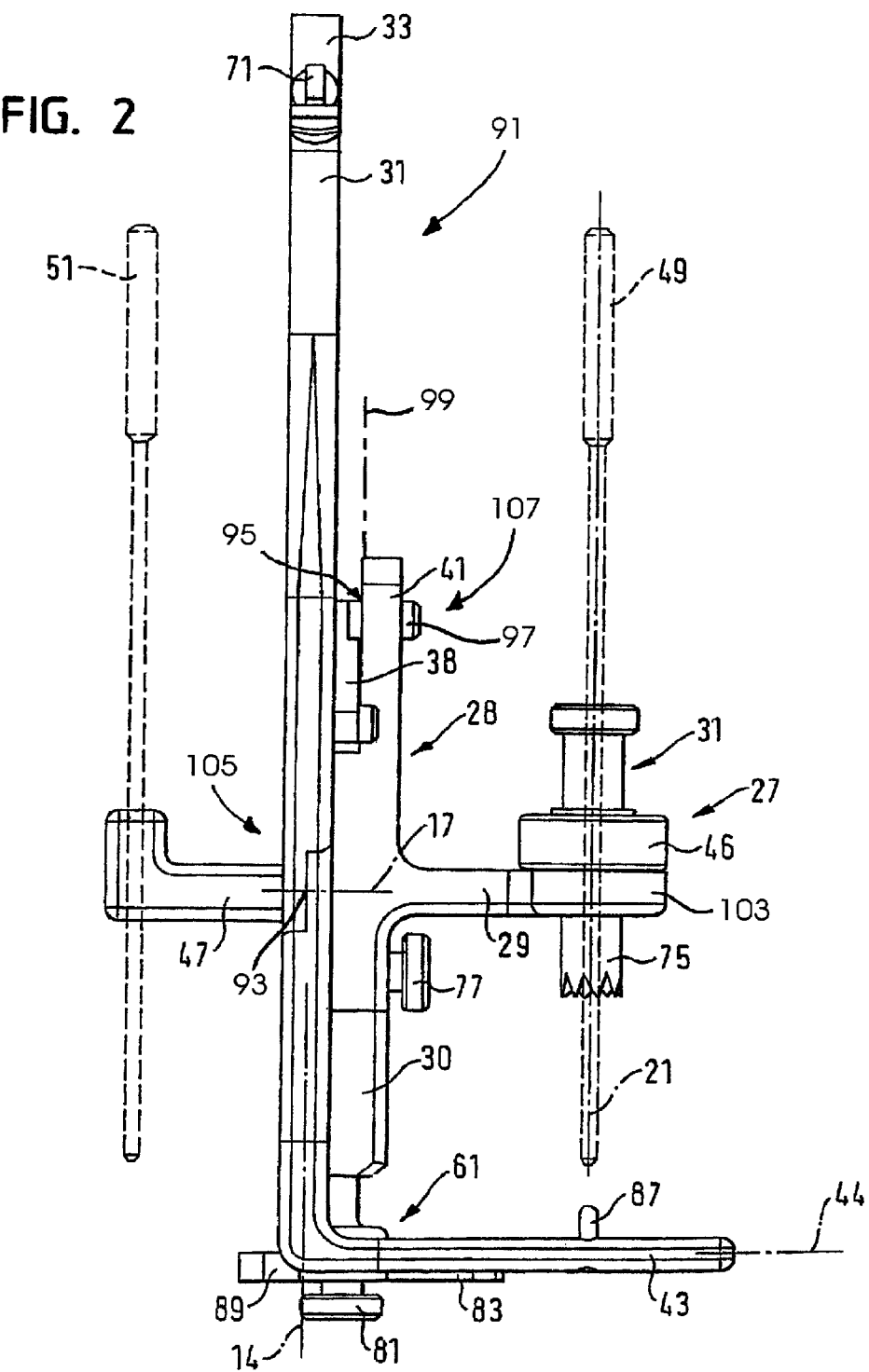
Figure 3:
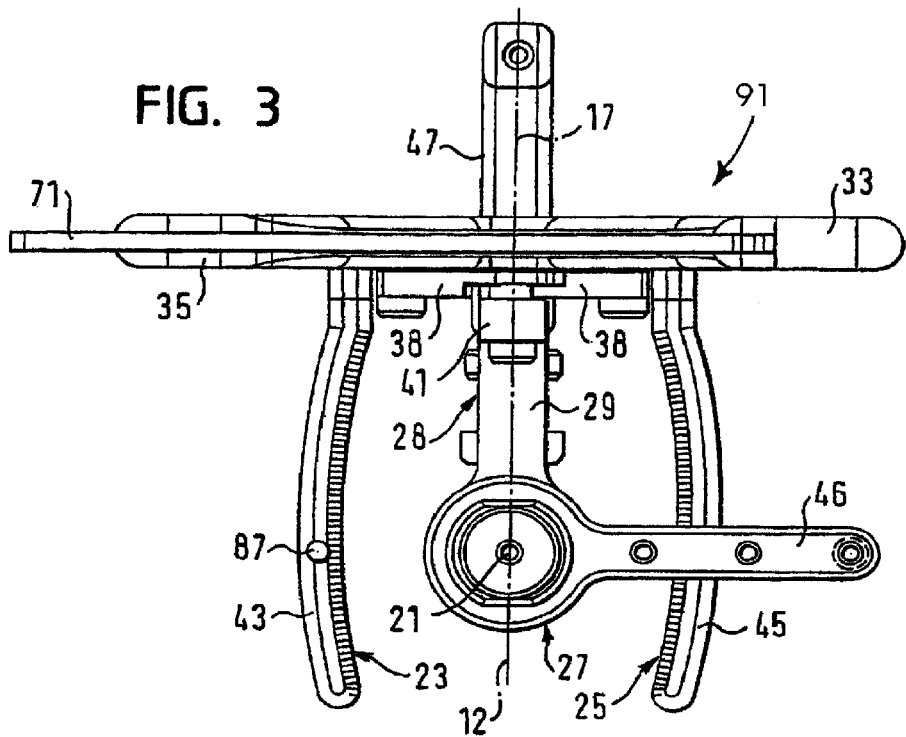
Figure 4:
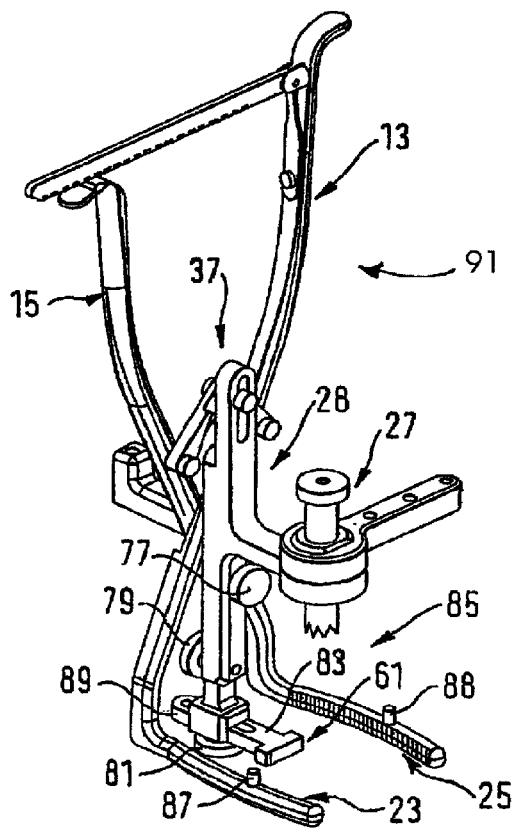

The embodiment of an instrument shown in FIGS. 1-5 includes probing forceps 91 with two probing levers or clamps 13, 15 which are pivotally connected to one another as in a pair of scissors or pliers at a fulcrum 93 shown in FIG. 2 which lies on a pivot axis 17 of the probing forceps 91, so that the two forcep levers 13, 15 can be mutually rotated relative to one another about the axis of rotation 17. The instrument is to this extent of X-like shape, with the pivot region which determines the axis of rotation 17 not lying at the center of the two forcep levers 13, 15, but rather dividing them approximately in the ratio of 1:2 to 1:3. Through the pivot axis 17 the instrument is divided into a manipulating side and a working side, with the manipulating side including actuation portions 33, 35 which will be explained subsequently in more detail and with the working side including probing portions 43, 45 which will be explained in more detail in the following.

One of the two longer upper actuating portions 33, 35 is provided with a latching arm 71, which is provided at its side facing the pivot axis 17 with a toothed latch arrangement, by which the latching arm 71 cooperates with the free end of the other actuating portion 35 in order to retain the respectively reached position during a closing movement by latching. The biasing of the latching arm 71 which is required for this is achieved by means of a spring 73 secured to the actuation portion 33.

The forcep levers 13, 15 span a lever plane 14 (FIG. 2) with probing portions 43, 45 extending perpendicular to it, and with the probing portions being formed at their mutually confronting inner sides as probing jaws 23, 25 which are set in front of the lever plane 14, with the lever plane being orientated in FIG. 2 perpendicular to the plane of the drawing. A central plane 12 of the probing forceps 91 and the lever plane 14 spanned by the two forcep levers 13, 15 stand perpendicular to one another, with the central plane 12 in FIG. 1 being orientated perpendicular to the plane of the sheet.

A guide element 28 and a rear aiming outrider 47 are located on different sides of the lever plane 14 and are connected to one another by means of a plug connection extending through bores in the forcep levers 13, 15 in the pivot region. The plug axis coincides with the pivot axis 17. The rear aiming outrider 47, which is stationary relative to the centering axis 21, has an angled end piece through which an aiming bar 51 indicated in broken lines in FIGS. 1 and 2 can be pushed which extends parallel to the lever plane 14 and lies in a central plane 12 (FIG. 1) which will subsequently be explained in more detail in the following.

The guide element 28 has a T-shaped basic shape, with the perpendicular leg of the "T" being formed by a carrier arm 29 for a centering axis 21 and for a functional unit 27, which will subsequently be explained in more detail, that extends along the pivot axis 17 and perpendicular to the lever plane 14. The upper part of the cross beam of the "T" which is disposed on the actuation side of the pivot axis 17 is provided with a linear guide 41 in the form of an elongate slot which extends parallel to the lever plane 14 and lies in the central plane 12 (FIG. 1). The linear guide 41 and the probing jaws 23, 25 are located on different sides of the pivot region. The central plane 12 extends through the axis of rotation 17 and centrally between the two forcep levers 13, 15. The ends of two guide levers 38 which are pivotally connected to one another via a fulcrum point 95 are compulsorily guided along the elongate slot guide 41 and are respectively connected at the other ends to the two forcep levers 13, 15. The fulcrum 95 is determined by a pin 97.

Consequently, the guide element 28 is journalled at a bearing point 105 at the fulcrum 93 and at a guide point 107 at the fulcrum 95.

Through this geometry a situation is achieved in which the two probing jaws 23, 25 of the forcep levers 13, 15 each have the same spacing from the central axis 21 independently of the pivotal position of the two forcep levers 13, 15. This signifies that the plane of symmetry of an article held by the two probing jaws 23, 25 always coincides with the central axis 21 of the instrument independently of how far the instrument has been opened.

The lower part of the cross beam of the "T" lying on the working side of the pivot axis 17 is essentially formed by a separate extension 30 which is held at the guide element 28 by a clamping screw 77. An auxiliary abutment 61 is held at the extension 30 by means of a further clamping screw 79 (FIG. 4) and is adjustable in the central plane 12 parallel to the lever plane 14. The auxiliary abutment 61 has a separate abutment element 83 which is in turn adjustable in the central plane 12, now however perpendicular to the lever plane 14 and thus parallel to a probing plane 44 (FIG. 2) spanned by the probing sections 43, 45 of the forcep levers 13, 15, with the probing plane 44 in FIG. 2 being orientated perpendicular to the sheet plane. The abutment element 83 is held at the auxiliary abutment 61 by means of a further clamping screw 81.

Two aiming pins 87, 88 are each arranged on a respective probing jaw 23, 25. Their connection line stands perpendicular to the central plane 12 and crosses the central axis 21. The probing jaws 23, 25 are so displaced when closing the instrument that they lie, when viewed from the side, approximately at the center of a neck 19 of the femur shown in FIG. 5. The abutment element 83 is displaceably adjustable perpendicular to the connection line of the aiming pins 87, 88. It has a scale 89 which respectively indicates the double distance (in numbers) from the auxiliary abutment 61 to the connection line of the aiming pins 87, 88. When the neck diameter is present in numbers in the central plane 12—for example through a prior measurement with a sliding caliper—then this diameter can be set in numbers with the scale 89 and the auxiliary abutment 61 ensures that the later drilling axis 21 coincides with the neck axis 101 at least in the region of the probing jaws 23, 25.

A functional unit 27 carried by the guide element 28 at the free end of the carrier arm 29 which includes a front aiming outrider 46 and also a drilling jig 31 is mounted in front of the lever plane 14 and is connected to the forcep levers 13, 15 via the carrier arm 29 lying in the central plane 12. The functional unit 27 and the probing jaws 23, 25 are located on the same side of the lever plane 14.

The free end of the carrier arm 29 is formed as a circular ring-like guide region 103 for the drilling jig 31. The front aiming outrider 46 is pivotally and releasably pushed onto this end with a likewise circular ring-like portion, with the projecting aiming arm of the aiming outrider being provided with a plurality of bores which extend parallel to the lever plane 14 and thus perpendicular to the probing plane 44. The bores serve to receive a further aiming bar 49.

The drilling jig is a centering sleeve 31 which is guided through the circular ring portions of the front aiming outrider 46 and of the guide region 103 of the guide element 29. The lower end side of the centering sleeve 31 is provided with fixing means, a toothed or serrated rim, which forms a fixing portion 75. Instead of a serrated rim, pointed projecting pins can also be provided. Furthermore, the centering sleeve 31 has a central through-bore which determines the drilling axis 21, which lies in the central plane 12 and extends parallel to the lever plane 14 and thus perpendicular to the probing plane 44. The aiming bars 49, 51 and a drilling instrument which is not shown but which is pushed through the centering sleeve 31, for example a Kirchner wire, thus extend parallel to one another.

In the state (FIG. 5) mounted on the femur, the probing sections 43, 45 contact the femur neck 19. The femur head 11 is located in a receiving space 85 of the instrument which is bounded at one side by the probing plane 44 (FIG. 2), at the opposite side by the functional unit 27 and perpendicular thereto by the lever plane 14 (FIG. 2). Thus the instrument requires very little space in the region of the femur head 11.

Figure 5:
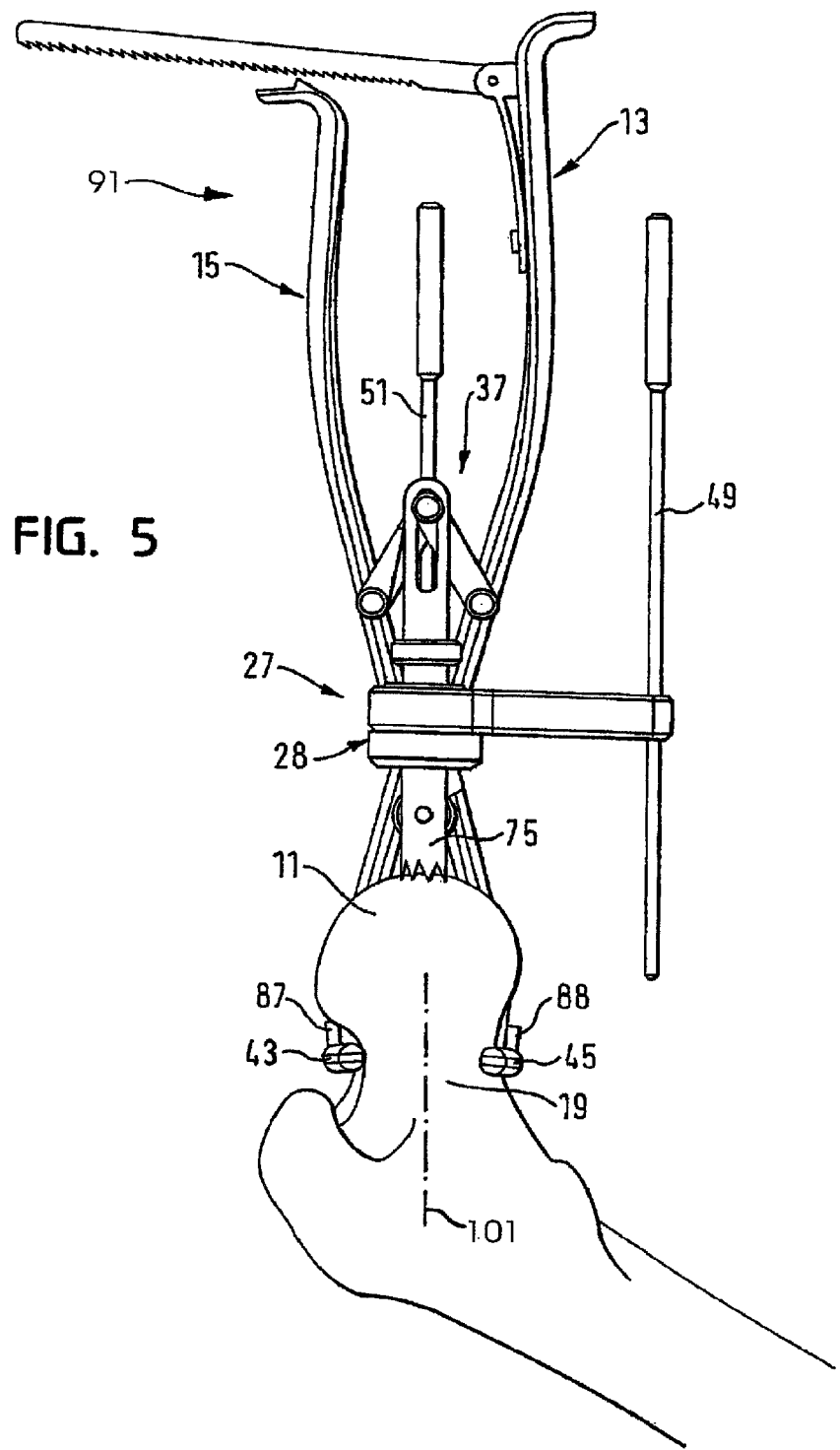
FIG. 5 shows the instrument of FIGS. 1-4 at a femoral head to be machined.

Not shown in FIG. 5 is the auxiliary abutment 61 (FIG. 4) the abutment element 83 of which lies in the probing plane 44 (FIG. 2). The free end of the abutment element 83 is thus likewise located at the level of the neck 19 of the femur and thus makes an additional alignment aid available.

The instrument serves for the determination of the position and direction of a bore which is to be formed in the femoral head 11 for a guide element, which is in particular wire-like or pin-like, along which instruments can subsequently be guided for the machining of the femoral head 11. Using the instrument, the operator can probe the transition between the femoral head 11 and the neck 19 of the femur via the probing jaws 23, 25 formed on the probing portions 43, 45 and in this connection operates advantageously and in space-saving manner from above.

The alignment of the instrument at the femur can be checked with the aid of the aiming bars 49, 51 of which the front aiming bar 49 disposed on the same side of the lever plane 14 as the functional unit 27 can be pivoted about the drilling axis 21. It is of particular advantage that this checking can take place with the two aiming bars 49, 51 in two planes standing perpendicular to one another. On reaching the desired position, the instrument can be fixed via the fixing portion 75 on the femur head by slight hammer blow on the centering sleeve 31.

The operation of the instrument is extremely simple for the operator and can take place with one hand. The latching of the achieved closing position which takes place during a closing movement can be released by slight lifting of the latching arm 71 in order to be able to reopen the instrument and set it in place anew if required. The auxiliary abutment 61 secures the instrument against tilting in the central plane 12. A rough pre-adjustment of the auxiliary abutment 61 can take place as a result of the operation planning.

The compulsory coupling of the actuation side portions of the forcep levers 13, 15 via the guide lever 38 with the linear guide extending in the central plane 12 automatically ensures a symmetrical opening and closing of the instrument with respect to the centering axis 21. In this way it is ensured that the drilling axis 21 lies in this central plane 12 in which the axis 101 of the neck of the femur lies, at least approximately, when the probing jaws 23, 25 contact the neck 19 of the femur or the start of the neck.

If the correct alignment of the instrument at the femoral head 11 has been found, then the centering on the femoral head 11 of the centering sleeve 31 can take place by blows on the centering sleeve which is provided at the bottom with serrations or with pointed pins, whereby the instrument is adequately reliably fixed to the femoral head 11 in order to introduce the desired bore in the femoral head through the central bore of the centering sleeve 31 along the aligned drilling axis 21.

Figure 6:
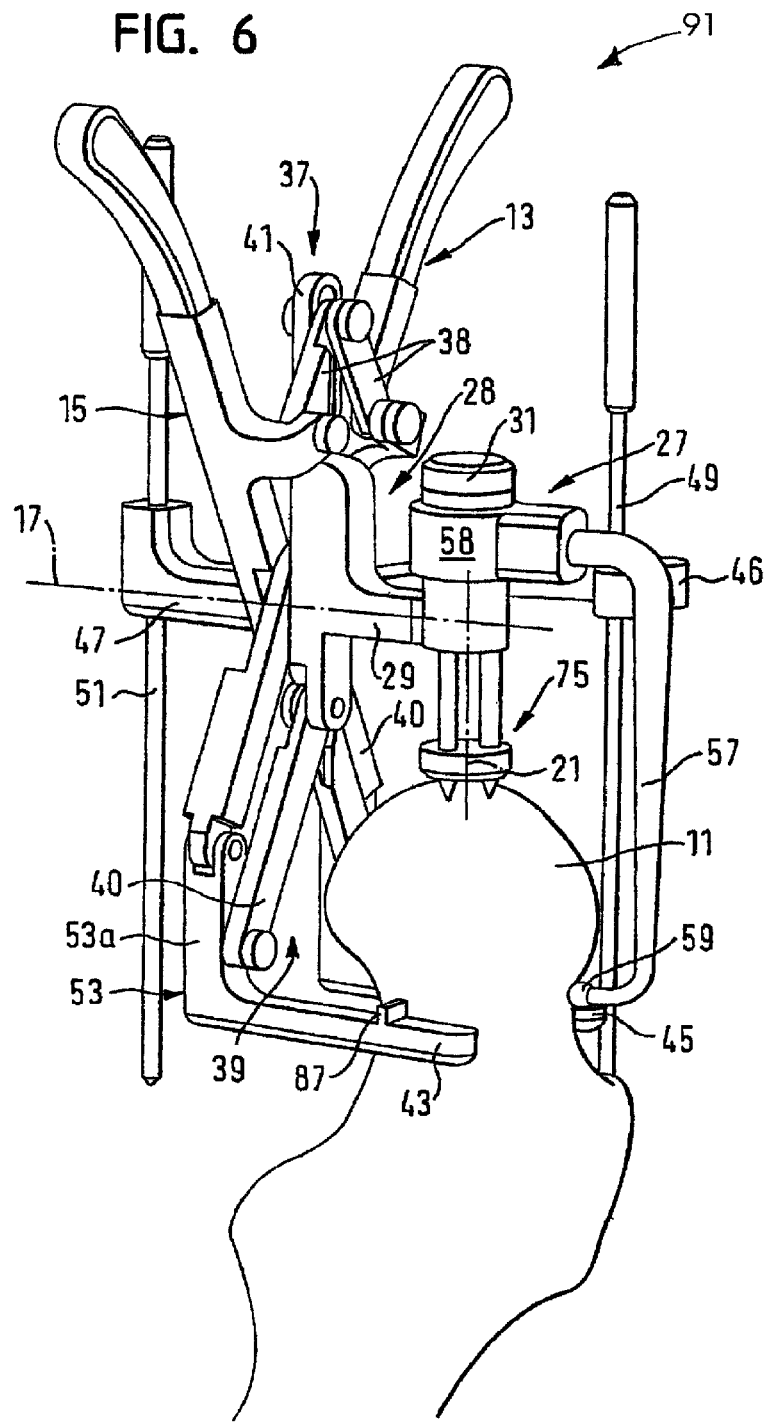
FIGS. 6 and 7 show various views of a further embodiment of an instrument.
Figure 7:
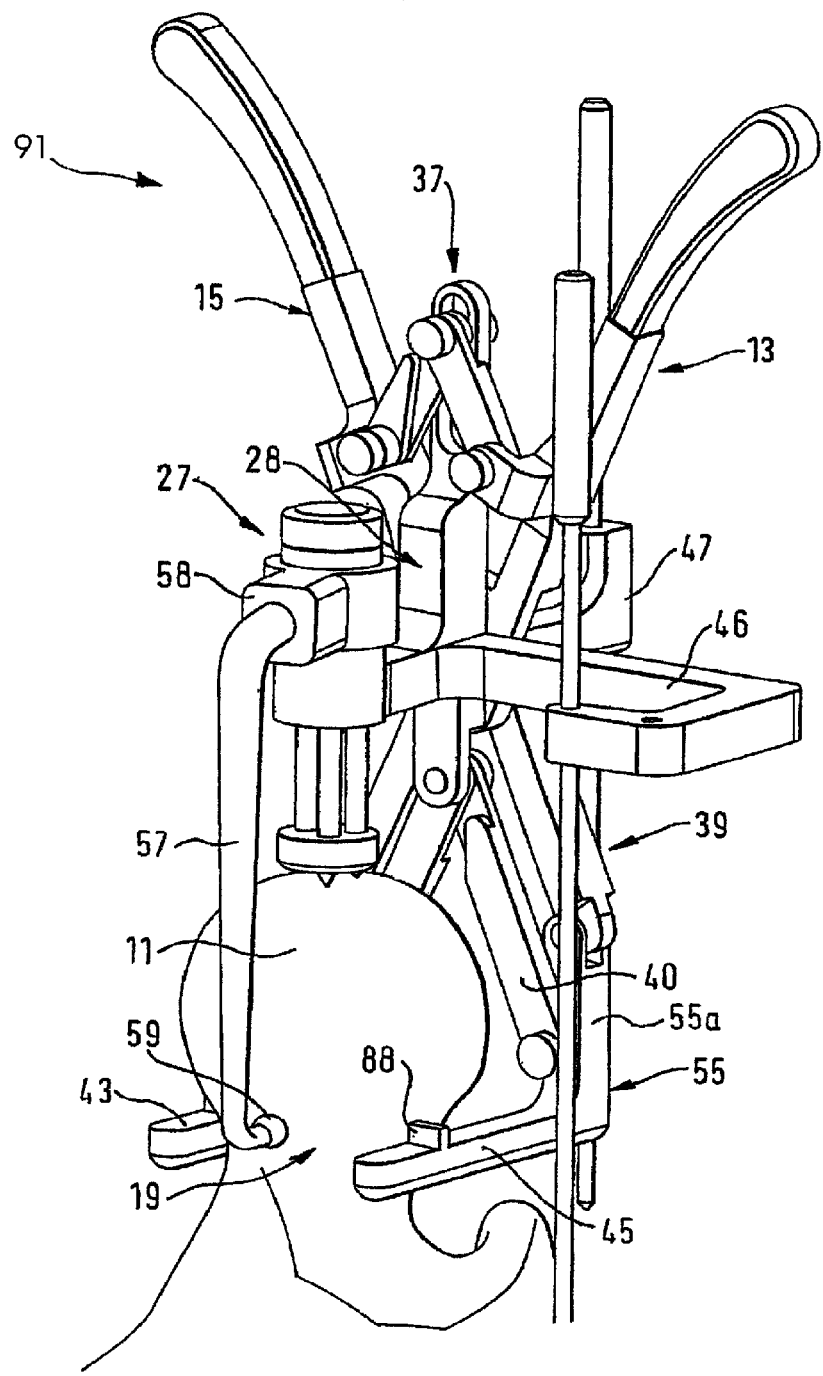

A further embodiment of an instrument in accordance with FIGS. 6 and 7 is distinguished from the previously explained embodiment firstly in that the probing portions 43, 45 are provided on the pivotable end portions 53, 55 of the forcep levers 13, 15, i.e. the forcep levers 13, 15 are not made rigid over their entire length but are provided with a hinge. The pivot axes of the end portions 53, 55 extend perpendicular to the lever plane 14 shown in FIG. 2.

The pivotal movement of the end portions 53, 55 is compulsorily guided by a further articulated arrangement 39 disposed below the pivot axis 17 which is formed as a parallelogram linkage. Two guide levers 40, which are respectively pivotally connected at their one end to a part section 53a, 55a of the pivotable end portion 53, 55 extending parallel to the lever plane 14, are jointly pivotally connected at their two other ends to the guide element 28.

A straight connecting line between the common hinge point for the two guide levers 40 and the pivot axis 17, i.e. the fulcrum 93 of the probing forceps 91 which lies in the central plane 12 explained in connection with FIG. 1, extends parallel to the part sections 53a, 55a, whereas the guide levers 40 respectively extend parallel to that part of the forcep lever 13, 15 which extends between the pivot axis 17 and the hinge point of the pivotable end portion 53, 55. In this way a four bar linkage in the form of a parallelogram is formed on each side of the central plane 12. During opening and closing of the instrument the two part sections 53a, 55a of the pivotable end portions 53, 55 thus extend during opening and closing of the instrument always parallel to one another independently of the pivotal position of the two forcep levers 13, 15.

Furthermore, in this embodiment, the front aiming outrider 46 for the front end bar 49 is not pivotable but it rather forms a rigid arm of the guide element 28. The aiming outrider 46 is of U-shape or hook-like shape, lies in a plane extending parallel to the probing plane 44 explained in conjunction with FIG. 2 and is guided around a pivot region for a probing arm 57 which will be described in more detail in the following The U-shaped probing arm 57, the open side of which faces the centering axis 21, is a component of the functional unit 27 and is pivotally mounted by means of a pivot part 58 above the pivot axis 17 around the drilling axis 21. The probing arm 57 extends downwardly in trunk-like manner until shortly above the probing plane 44 spanned by the probing sections 43, 45 and in doing so around the receiving region 85 (FIG. 4) of the instrument for the femoral head 11.

At the free end of the probing arm 57 a spherical probing head 59 is formed approximately at the level of the probing jaws 23, 25. By pivoting of the probing arm 57 the so-called "circular tracing" can be carried out in which the probing head 59 is guided around the drilling axis 21 along the start of the neck of the femoral head 11 in order to check the position of the instrument in a direction extending parallel to the pivot axis 17 and relative to the femoral head 11. In this connection the instrument with the probing sections 43, 45 is fixed below the start of the neck at the femur so that the probing head 59 can move at the level of the start of the neck during the circular tracing.

Furthermore, in distinction to the above-explained embodiment, the fixing portion 75 is not provided here in the form of a "crown-like" end face of a sleeve. On the contrary the fixing portion 75 is formed here by three parallel pins which converge to a point of the bottom and which are arranged equally spaced from one another in the peripheral direction at the same radial spacing from the drilling axis 21.

A circular tracing unit in accordance with the embodiment of FIGS. 6 and 7 can also be provided in the embodiment of FIGS. 1 to 5. Furthermore, in both embodiments, the other respective centering sleeve 31 and/or the other respective fixing portion 75 can be provided. A parallelogram linkage with pivotable end portions corresponding to the embodiment of FIGS. 6 and 7 can also be provided in the embodiment of FIGS. 1 to 5.

Figure 8:
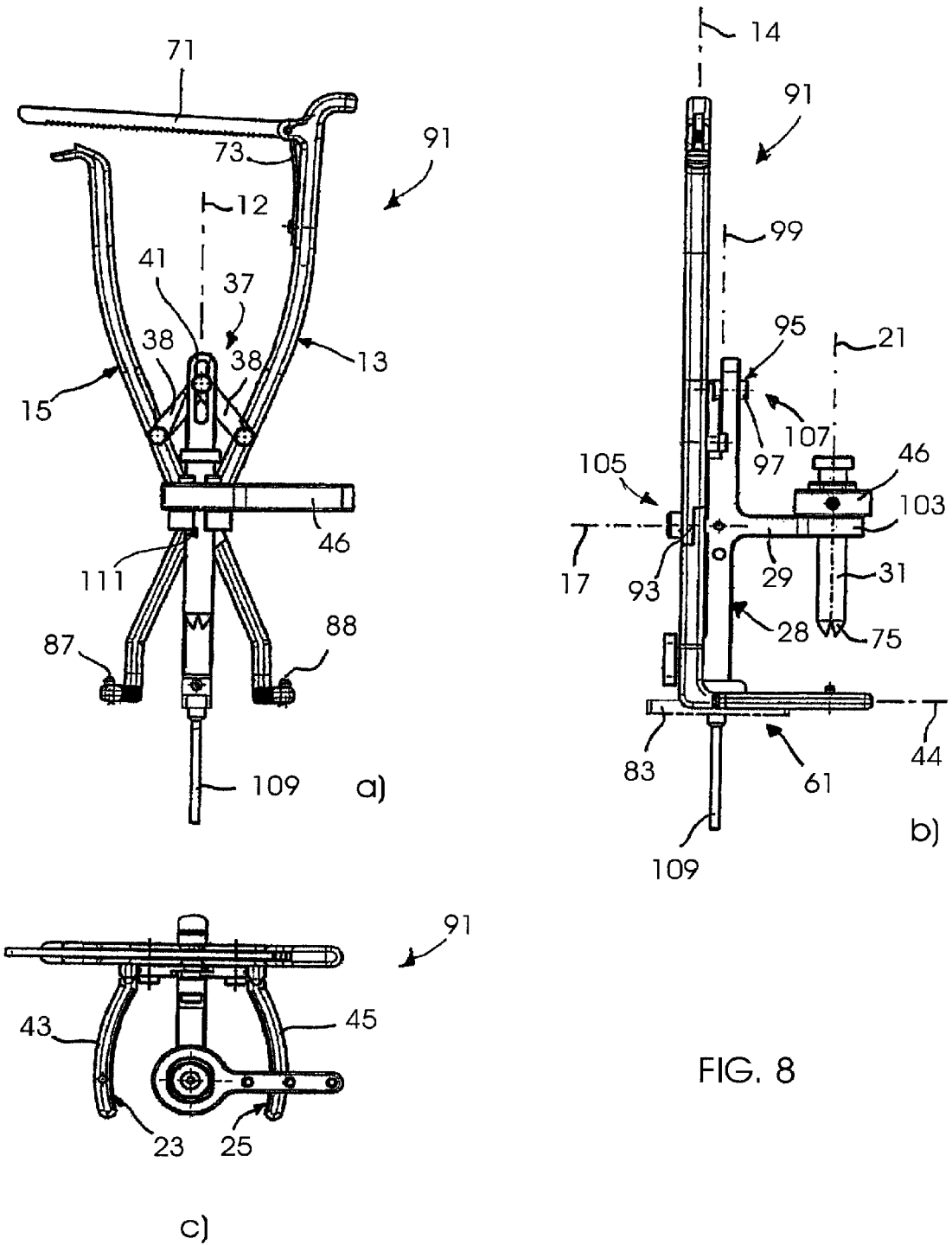
FIG. 8 shows various views of another embodiment of an instrument.
Figure 9:
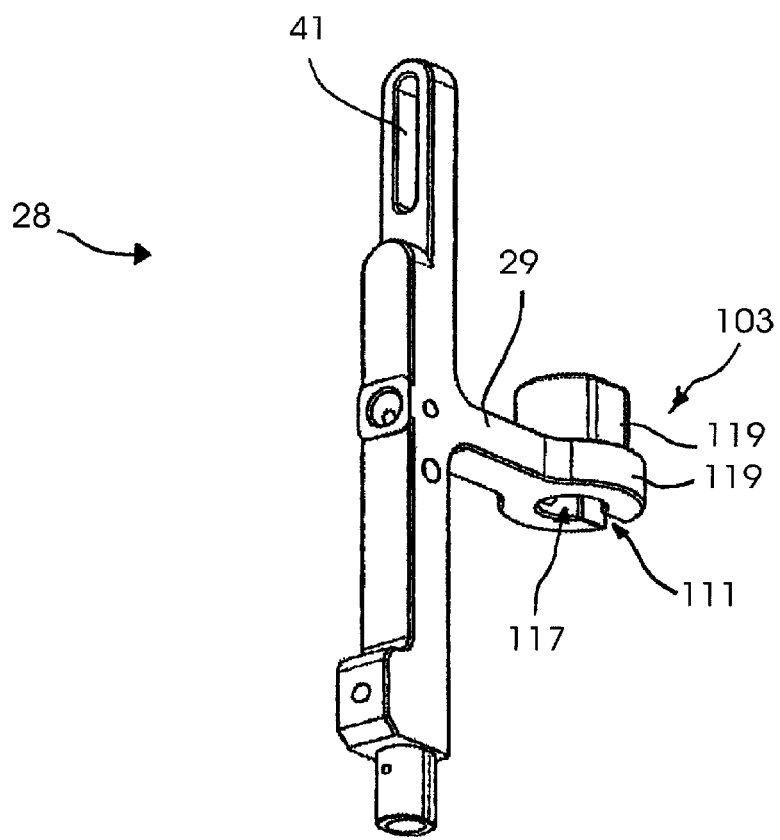
FIG. 9 shows a guide element of the instrument of FIG. 8.

Yet another embodiment of the instrument in accordance with FIG. 8 is distinguished from the previously explained embodiments first of all in that no rear aiming outrider and no rear aiming bar are provided in the pivot region of the probing forceps 91. Instead, a lower aiming bar 109 which can be coupled to the guide element 28 is provided in the axial extension of the guide axis 99 and extends in the state mounted to the guide element 28 beyond the ends of the forcep levers 13, 15. Moreover, a set of abutment elements 83 for the neck of the femur is provided instead of an abutment element adjustable perpendicular to the lever plane 14 and the abutment elements are respectively capable of being coupled to the guide element 28, with the abutment element 83 respectively mounted on the guide element 28 extending transversely to the centering axis 21 and having a free abutment end remote from the centering axis. The abutment elements are distinguished at least in that in the state mounted on the guide element 28 their free abutment ends are spaced by different amounts from the centering axis 21. For the attachment to the guide element 28 the respective abutment element 83 is plugged onto the guide element 28 via a latch device and/or snap device, in particular via a ball latch. Furthermore, the embodiment of FIG. 8 is distinguished from the previously explained embodiments by the guide region 103. The guide region 103 of the embodiment of FIG. 8 admittedly includes, as do the previously explained guide regions, a mount 117 for the centering sleeve 31, with the mount 117 being bounded by a wall section 119 of the guide region 103, as can be seen in FIG. 9. However, the guide region 103 of the embodiment of FIG. 8 is slotted, i.e. a slit 111 is provided in the wall section 119 in such a way that the wall section 119 only partly surrounds the mount 117.

Otherwise the other embodiment of the instrument in accordance with FIG. 8 is formed essentially analogously to the previously explained embodiments, with some of the common features being repeated again below and/or being illuminated from a different perspective. Thus, in the instrument in accordance with FIG. 8 the centering axis 21, the mounting point 105 hinged to the fulcrum 93 and the guide point 107 arranged at the hinge point 95 always lie in the central plane 12 of the probing forceps 91 independently of the opening angle of the probing forceps 91. Moreover, the guide axis 99 determined by the mounting point 105 and the guiding point 107 is likewise orientated parallel to the centering axis 21. Furthermore, a pair of guide levers 28 of the same length is likewise provided which are arranged symmetrically to the central plane 12 which are each rotatably connected to one of the forcep levers 13, 15 and also to one another at a hinge point 95, with the guide point 107 being arranged at the hinge point 95 which connects the guide levers 38 to one another. Furthermore, the guide element 28 likewise has an elongate hole 41 with the articulated connection between the guide levers 38 being formed by a pin 97 which is guided in the elongate hole 41 of the guide element 28. Furthermore, the guide levers 38 are likewise pivotally connected at the manipulation side of the probing forceps 91 to the forcep levers 13, 15. Furthermore, the guide element 28 likewise includes a guide region 103 for a centering element 31, in particular a centering sleeve, which specifies the centering axis 21. Furthermore, the centering element 31 is likewise displaceable in the direction of the centering axis 21. Furthermore, the centering element 31 likewise includes fixing means 75 at one end for the fixing of the instrument to the femoral head 11, with the fixing means in particular being arranged towards the working side. Furthermore, the guide region 103 is likewise formed at a carrier arm 29 of the guide element 29 extending transverse to the centering axis 21. Furthermore, the guide region 103 is likewise capable of being coupled to an aiming outrider 46 and to an aiming bar 49 associated with the aiming outrider 46 and/or to an adapter device 113 shown in the FIGS. 10 to 12 to fix a drilling axis 115 inclined relative to the centering axis 21. Furthermore, latching means 71 are likewise provided by which the forcep levers 13, 15 can be adjustably fixed to one another in their relative position. Furthermore, the latching means likewise include a latching arm 71 which is pivotally connected to the one forcep lever 13 and can be releasably latched to the other forcep lever 15 via an adjustable toothed latch.

Figure 10:
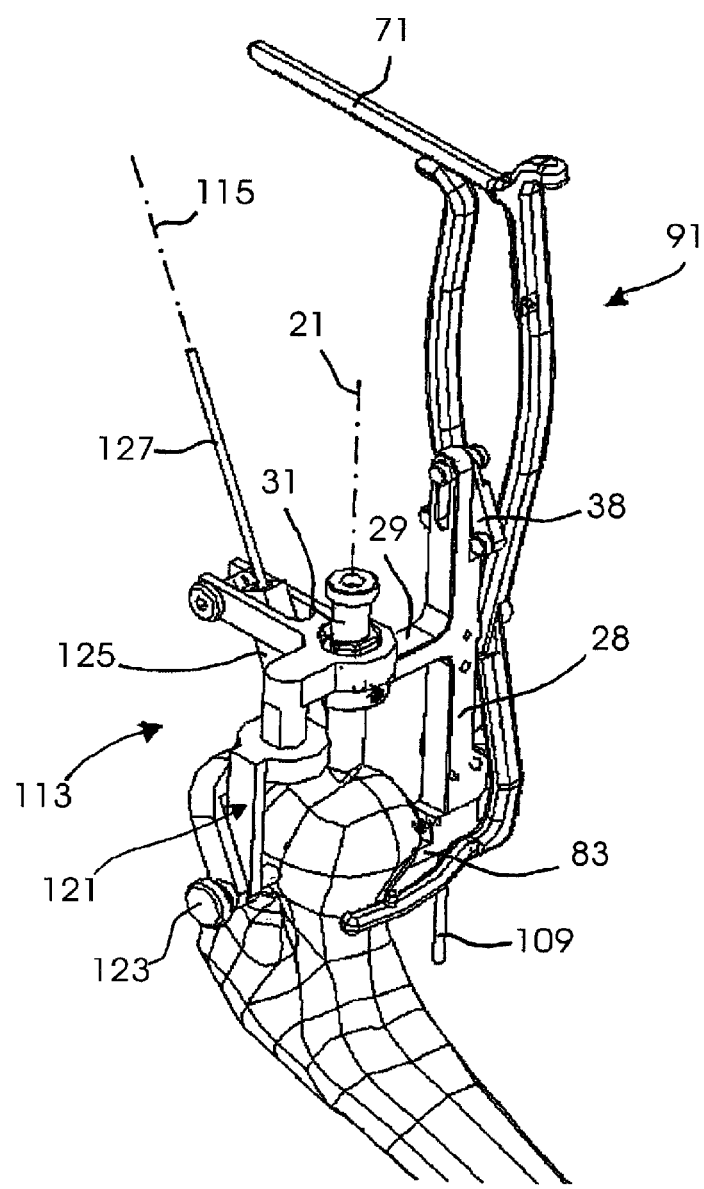
FIGS. 10-12 show the instrument of FIG. 8, each with an adapter device.
Figure 11:
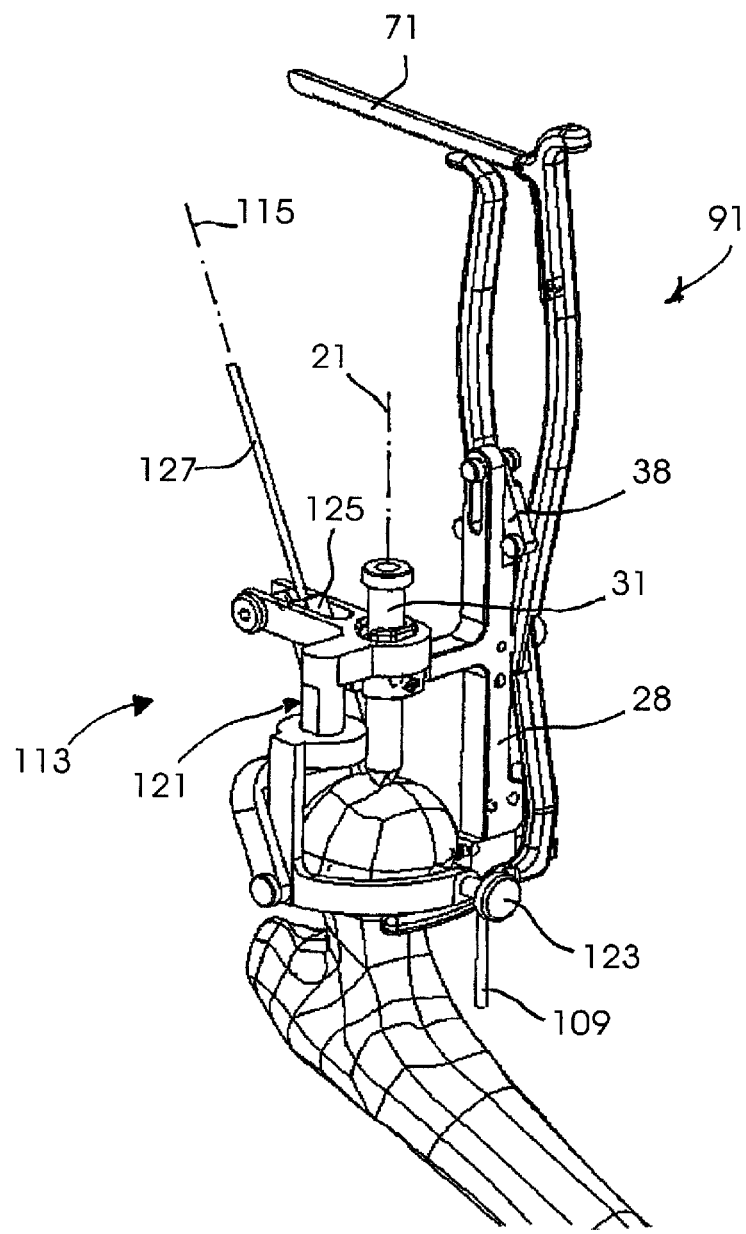
Figure 12:
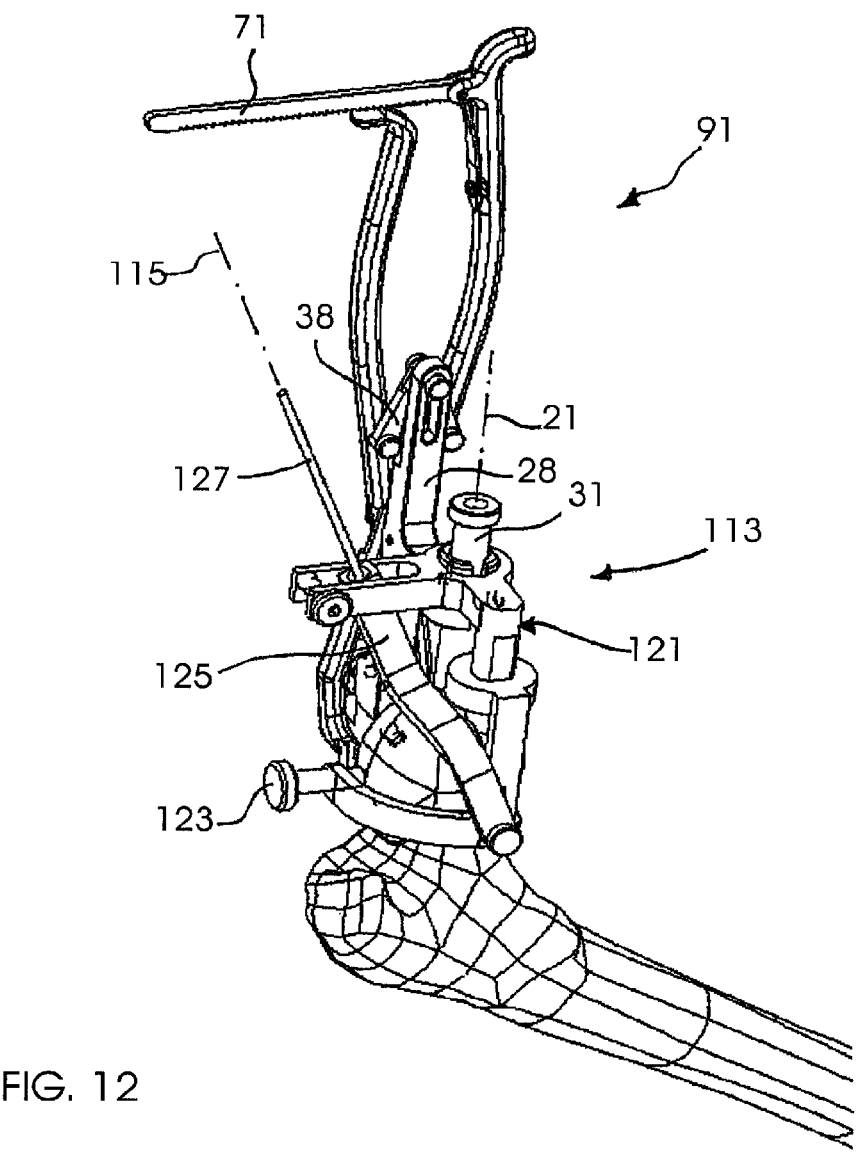

The FIGS. 10 to 12 show the instrument from FIG. 8 with an adapter device 113 through which a drilling axis 115 inclined relative to the centering axis 21 can be fixed. The adapter device 113 includes first of all a probing device 121 with a probing element 123 for the probing of the femoral head 11. The probing device 121 is, in this arrangement, formed in such a way that the probing element 123 is adjustable in a direction parallel to the centering axis 121. In this way it is made possible for the probing element 123 to be placed at different points on the femoral head 11. The probing element 123 is arranged in such a way that a probing of the femoral head 11 takes place from anterior.

Moreover, the adapter device 113 includes elongate guide means 125 coupled to the probing device 121 for the guidance of a drilling wire 127 for the generation of a bore in the femoral head 11 along the drilling axis 115. The longitudinal axis of the guide means 125 is in this arrangement orientated such that the drilling axis 115, the centering axis 21 and a probing plane extending perpendicular to the centering axis 21, in which a free end of the probing element 123 lies, intersect at a point. The inclination of the drilling axis 115 relative to the centering axis 21 is steplessly adjustable in this arrangement.

Through the inclined drilling axis 115 it is made possible to mount an implant tilted relative to the axis 101 of the femur neck, in particular a tilted cap-like implant, on the femoral head 11. As can be recognized in particular with reference to the FIGS. 11 and 12, not only one probing device 121 is provided but rather a set of probing devices 121 with the probing devices 121 being at least distinguished in that the probing of the femoral head 11 takes place in FIG. 10 by a probing element 123 disposed anterior, in FIG. 11 by a probing element 123 arranged distal and in FIG. 12 by a probing element 123 arranged proximal.

In the following an exemplary procedure for the fixing of the centering axis 21 and also for any required fixing of the drilling axis 115 which can be optionally inclined relative to the centering axis is described with reference to the drawings.

First of all, the diameter of the neck 19 of the femur is determined, for example by means of a caliper. Thereafter an abutment element 83 matching the diameter of the neck 19 of the femur is selected from a set of different abutment elements 83 and is mounted on the instrument. Thereafter the instrument is set in place and aligned at the femoral head or at the neck of the femur such that the neck 19 of the femur comes into abutment at the abutment element 83 of the instrument matched to the diameter of the neck 19 of the femur in order to align the centering axis 21 in the center with respect to the mounting side of the instrument and at its opposite side, in particular in the anterior-posterior direction. The probing forceps 91 of the instrument are subsequently closed such that the probing jaws 23, 25 symmetrically contact the neck 19 of the femur at opposite sides with respect to the axis 101 of the femur neck, in particular proximally and distally in order to automatically centrally align the centering axis 21 with respect to the two oppositely disposed sides of the femur neck 19. On the whole this is achieved in that after the closing of the probing forceps 91 the centering axis 21 coincides with the axis 101 of the femur neck.

Thereafter the inclination of the centering axis 21 is checked and if necessary corrected by means of the front aiming bar 49 and also the CCD angle is checked and if necessary corrected by means of the rear aiming bar 51 or the lower aiming bar 109. Thereafter the forcep levers 13, 15 are fixed in their relative position to one another and the instrument is fixed in the aligned position at the femoral head 11 by means of the centering sleeve 31 which determines the centering axis 21, for example by a light hammer blow on the centering element 31.

If the bore to be produced in the femoral head 11 is to coincide with the axis 101 of the neck of the femur a drilling wire is first inserted through the centering sleeve 31 along the centering axis 21 into the femoral head 11. The drilling wire can previously have been used in one embodiment of the method as the front aiming bar 49. Thereafter the front aiming outrider 46 coupled to the instrument through which the drilling wire passes and also the centering sleeve 31 which serves for the guiding of the drilling wire are unthreaded along the drilling wire from the drilling wire and removed. Finally the instrument is removed transverse to the longitudinal extent of the drilling wire, with the drilling wire being guided through the slot 111 formed at the instrument. The mounted drilling wire can now be used for the orientation of a tool for the machining of the femoral head 11.

If the bore to be produced in the femoral head 11 does not however coincide with the axis 101 of the femoral neck but is rather inclined relative to the centering axis 21 the instrument is coupled to the adapter device 113. Thereafter the femoral head 11 is probed with the probing device 121 of the adapter device 113 in order to determine an equatorial plane of the femoral head 11 perpendicular to the centering axis 21. Thereafter the inclination of the drilling axis 115 relative to the centering axis 21 is fixed, with the drilling axis 115 being aligned in such a way that it extends through the intersection point of the equatorial plane with the centering axis 21. In this way it is made possible that the drilling axis 115 is orientated in the direction of the ball center of the femoral head 11. Next the drilling axis 115 inclined relative to the centering axis 21 is fixed relative to the instrument. Thereafter the drilling wire 127 is inserted along the drilling axis 115 into the femoral head 11. Finally, the adapter device 113 and the instrument are removed from the femoral head 11. The placed drilling wire 127 can now be used for the orientation of a tool for the machining of a femoral head 11.

The described instrument enables in particular specific methods which will be described in the following for the preparation and/or machining of a femoral head to be carried out.

A method for the preparation and/or machining of a femoral head which is formed on a neck of a femur and which has an axis of a femur neck includes selecting an instrument for the preparation and/or machining of the femur head which includes probing forceps with two forcep levers and two probing jaws and also a guide element with a centering axis which always lies in a central plane of the probing forceps independent of an opening angle of the probing forceps and closing the probing forceps in such a way that the probing jaws symmetrically contact the neck of the femur at opposite sides with respect to the axis of the neck of the femur, in particular proximally and distally, whereby the centering axis is automatically aligned in the middle with respect to the two oppositely disposed sides of the femur neck.

A further method further includes the selection of an instrument which is an instrument in accordance with at least one of the claims.

A further method further includes aligning the instrument prior to closing of the probing forceps such that the neck of the femur comes into abutment, in particular posterior, at an abutment element of the instrument matched to the diameter of the neck of the femur, so that after the closing of the probing forceps the centering axis coincides with the axis of the neck of the femur.

A further method further includes selecting an abutment element matched to the diameter of the femur neck from a set of different abutment elements prior to the alignment of the instrument.

A further method further includes determining the diameter of the neck of the femur prior to the selection of the abutment element matched to the diameter of the neck of the femur.

A further method further includes checking and/or correcting the inclination of the centering axis by means of an aiming bar and checking and/or correcting the CCD angle by means of a further aiming bar.

A further method further includes fixing the forcep levers in their relative position to one another.

A further method further includes fixing the instrument in an aligned position at the femur head by means of the centering element fixing the centering axis.

A further method further includes inserting a drilling wire into the femur head along the centering axis through a centering element formed as a centering sleeve.

A further method further includes unthreading and removing from the drilling wire an aiming outrider through which the drilling wire passes and previously coupled to the instrument for checking the inclination of the centering axis and/or to unthread and remove the centering sleeve serving for the guidance of the drilling wire along the drilling wire from the drilling wire.

A further method further includes removing the instrument transverse to the longitudinal extent of the drilling wire, with the drilling wire being passed through a slot formed at the instrument.

A further method further includes coupling the instrument to an adapter device which includes means for fixing the drilling axis inclined relative to the centering axis.

A further method further includes fixing the inclination of the drilling axis relative to the centering axis.

A further method further includes fixing relative to the instrument the drilling axis inclined relative to the centering axis.

A further method further includes inserting a drilling wire into the femur head along the drilling axis.

A further method further includes probing the femoral head with a probing device of the adapter device in order to determine an equatorial plane of the femoral head extending perpendicular to the centering axis.

A further method further includes aligning the drilling axis in such a way that it extends through the intersection point of the equatorial plane with the centering axis.

The features set forth for the method of the operation can also be combined with one another.

In the light of the explanations given here further embodiments will be made available to the person skilled in the art of the invention characterized in the claims which cannot be exhaustively portrayed here.

REFERENCE NUMERAL LIST 11 femoral head
12 central plane
13 forcep lever, clamp
14 lever plane
15 forcep lever, clamp
17 pivot axis
19 neck of femur
21 centering axis, drilling axis
23 probing jaw
25 probing jaw
27 functional unit
28 guide element
29 carrier arm
30 extension
31 drilling jig, centering sleeve
33 actuating portion
35 actuating portion
37 articulated lever arrangement
38 guide lever
39 articulated lever arrangement, parallelogram linkage
40 guide lever
41 linear guide, elongate hole
43 probing portion
44 probing plane
45 probing portion
46 front aiming outrider
47 rear aiming outrider
49 front aiming bar
51 rear aiming bar
53 pivotable end portion
53a part section
55 pivotable end portion
55a part section
57 probing arm
58 pivot part
59 probing head
61 auxiliary abutment
71 latching arm
73 spring
75 fixing portion
77 clamping screw
79 clamping screw
81 clamping screw
83 abutment element 85 receiving space
87 aiming pin
88 aiming pin
89 scale
91 probing forceps
93 fulcrum
95 hinge point
97 pin
99 guide axis
101 axis of the neck of the femur
103 guide region
105 mounting point
107 guide point
109 lower aiming bar
111 slot
113 adapter device
115 drilling axis
117 mount
119 wall section
121 probing device
123 probing element
125 guide means
127 drilling wire

What is claimed is:

1. A method for at least one of preparation or machining of a femoral head formed on a neck of a femur including an axis of the neck of the femur, the method comprising:
    selecting an instrument for at least one of the preparation or the machining of the femoral head, the instrument including:
        probing forceps including two forcep levers and two probing jaws, wherein the forcep levers are connected to each other at a fulcrum, each of the forcep levers including one of the probing jaws, the forcep levers each having a proximal end and a distal end, the proximal end being disposed away from the fulcrum; and
        a guide element including a centering axis, the guide element coupled to the probing forceps at first and second coupling points disposed along the centering axis such that the centering axis is disposed in a central plane of the probing forceps independent of an opening angle of the probing forceps; and
    closing the probing forceps with the probing jaws symmetrically contacting the neck of the femur at opposite sides with respect to the axis of the neck of the femur, wherein the guide element self-adjusts with closing of the probing forceps so that the centering axis is automatically aligned in the middle with respect to the two oppositely disposed sides of the neck of the femur.

2. The method of claim 1, wherein the instrument includes a pair of guide levers of equal length, wherein each of the forcep levers includes an actuation portion, the actuation portions being manually operable to move the forcep levers about the fulcrum, the guide levers each including a first end rotatably connected to a respective one of the actuation portions of the forcep levers, the guide levers including second ends rotatably connected to each other via a pin at the second coupling point, the actuation portions extending beyond the guide levers in a direction away from the fulcrum.

3. The method of claim 1, comprising aligning the instrument prior to closing of the probing forceps such that the neck of the femur comes into abutment with an abutment element of the instrument, so that after the closing of the probing forceps the centering axis coincides with the axis of the neck of the femur.

4. The method of claim 3, comprising matching the abutment element of the instrument to a diameter of the neck of the femur.

5. The method of claim 3, comprising selecting the abutment element matched to a diameter of the neck of the femur from a set of different abutment elements prior to the alignment of the instrument.

6. The method of claim 5, comprising determining the diameter of the neck of the femur prior to the selection of the abutment element matched to the diameter of the neck of the femur.

7. The method of claim 1, comprising:
    at least one of checking or correcting an inclination of the centering axis using a first aiming bar; and
    at least one of checking or correcting a caput-collum-diaphyseal (CCD) angle using a second aiming bar.

8. The method of claim 1, comprising fixing the forcep levers in a relative position to each other.

9. The method of claim 1, comprising fixing the instrument in an aligned position at the femoral head using a centering element to fix the centering axis.

10. The method of claim 1, comprising inserting a drilling wire into the femoral head along the centering axis through a centering element including a centering sleeve.

11. The method of claim 10, comprising at least one of:
    removing from the drilling wire an aiming outrider configured to check an inclination of the centering axis; or
    removing from the drilling wire the centering sleeve configured for guiding the drilling wire along the drilling wire.

12. The method of claim 10, comprising removing the instrument transverse to a longitudinal extent of the drilling wire, with the drilling wire being passed through a slot of the instrument.

13. The method of claim 1, comprising coupling the instrument to an adapter device configured to fix an inclination of a drilling axis relative to the centering axis.

14. The method of claim 1, comprising fixing an inclination of a drilling axis relative to at least one of the centering axis or the instrument.

15. The method of claim 1, comprising inserting a drilling wire into the femoral head along a drilling axis.

16. The method of claim 1, comprising probing the femoral head with a probing device to determine an equatorial plane of the femoral head extending substantially perpendicular to the centering axis.

17. The method of claim 16, comprising aligning a drilling axis to extend through an intersection point of the equatorial plane and the centering axis.

18. A method for at least one of preparation or machining of a femoral head formed on a neck of a femur including an axis of the neck of the femur, the method comprising:
    selecting an instrument for at least one of the preparation or the machining of the femoral head, the instrument including:
        probing forceps including two forcep levers and two probing jaws, wherein the forcep levers are connected to each other at a fulcrum, each of the forcep levers includes one of the probing jaws; and
        a guide element including a centering axis, the guide element coupled to the probing forceps at first and second coupling points disposed along the centering axis such that the centering axis is disposed in a central plane of the probing forceps independent of an opening angle of the probing forceps;
    selecting an abutment element matched to a diameter of the neck of the femur;

aligning the instrument such that the neck of the femur comes into abutment with the abutment element of the instrument; and closing the probing forceps with the probing jaws symmetrically contacting the neck of the femur at opposite sides with respect to the axis of the neck of the femur, wherein the centering axis is automatically aligned in the middle with respect to the two oppositely disposed sides of the neck of the femur, and wherein the centering axis coincides with the axis of the neck of the femur.

19. The method of claim 18, wherein selecting the abutment element includes selecting the abutment element from a set of different abutment elements prior to the alignment of the instrument.

20. The method of claim 18, comprising fixing the instrument in an aligned position at the femoral head using a centering element to fix the centering axis.

* * * * *